United States Patent
Hagemeyer et al.

(10) Patent No.: US 6,849,243 B1
(45) Date of Patent: Feb. 1, 2005

(54) CATALYSTS FOR THE GAS-PHASE OXIDATION OF ETHYLENE AND ACETIC ACID TO VINYL ACETATE, A PROCESS FOR PRODUCING THEM AND THEIR USE

(75) Inventors: Alfred Hagemeyer, Sunnyvale, CA (US); Harald Werner, Bad Homburg (DE); Uwe Dingerdissen, Seeheim-Jugenheim (DE); Klaus Kühlein, Kelkheim (DE); Günter Dambeck, Selters (DE); Gerhardt Geiss, Liederbach (DE); Andrea Rutsch, Mörfelden (DE); Stephan Weidlich, Frankfurt (DE)

(73) Assignee: Celanese Chemicals Europe GmbH (DE)

(*) Notice: Subject to any disclaimer, the term of this patent is extended or adjusted under 35 U.S.C. 154(b) by 0 days.

(21) Appl. No.: 09/937,524

(22) PCT Filed: Mar. 21, 2000

(86) PCT No.: PCT/EP00/02455
§ 371 (c)(1),
(2), (4) Date: Sep. 25, 2001

(87) PCT Pub. No.: WO00/58008
PCT Pub. Date: Oct. 5, 2000

(30) Foreign Application Priority Data

Mar. 27, 1999 (DE) .......................................... 199 14 066

(51) Int. Cl.$^7$ ........................ C01B 21/068; C01B 33/06
(52) U.S. Cl. ........................ 423/344; 423/333; 423/305
(58) Field of Search .............................. 502/305, 332, 502/333, 317, 344

(56) References Cited

U.S. PATENT DOCUMENTS

| | | | | |
|---|---|---|---|---|
| 3,761,513 A | * | 9/1973 | Sennewald et al. | 560/245 |
| 4,048,096 A | * | 9/1977 | Bissot | 502/170 |
| 4,087,622 A | * | 5/1978 | Nakamura et al. | 560/245 |
| 4,188,490 A | * | 2/1980 | Hinnenkamp et al. | 560/245 |
| 5,179,056 A | * | 1/1993 | Bartley | 502/170 |
| 5,179,057 A | * | 1/1993 | Bartley | 502/170 |
| 5,185,308 A | * | 2/1993 | Bartley et al. | 502/170 |
| 5,189,004 A | * | 2/1993 | Bartley | 502/170 |
| 5,314,858 A | * | 5/1994 | Colling | 502/330 |
| 5,336,802 A | * | 8/1994 | Smith et al. | 560/245 |
| 5,466,652 A | * | 11/1995 | Paparizos et al. | 502/330 |
| 5,591,688 A | * | 1/1997 | Blum et al. | 502/330 |
| 5,693,586 A | * | 12/1997 | Nicolau et al. | 502/330 |
| 5,700,753 A | * | 12/1997 | Wang et al. | 502/330 |
| 5,990,344 A | * | 11/1999 | Couves et al. | 560/245 |
| 6,225,496 B1 | * | 5/2001 | Baker et al. | 560/245 |
| 6,303,537 B1 | * | 10/2001 | Wang et al. | 502/330 |
| 6,346,501 B1 | * | 2/2002 | Herzog et al. | 502/304 |
| 6,358,882 B1 | * | 3/2002 | Salem et al. | 502/305 |
| 6,395,676 B2 | * | 5/2002 | Blum et al. | 502/330 |
| 6,399,813 B1 | * | 6/2002 | Blum et al. | 560/245 |
| 6,407,283 B2 | * | 6/2002 | Couves et al. | 560/245 |
| 6,492,299 B1 | * | 12/2002 | Couves et al. | 502/339 |
| 6,528,452 B1 | * | 3/2003 | Bergmann | 502/324 |
| 6,534,438 B1 | * | 3/2003 | Baker et al. | 502/325 |
| 6,534,672 B2 | * | 3/2003 | Salem et al. | 560/241 |

FOREIGN PATENT DOCUMENTS

| | | |
|---|---|---|
| EP | 0565952 | 10/1993 |
| EP | 0672453 | 9/1995 |
| EP | 0723810 | 7/1996 |
| EP | 0839793 | 5/1998 |

OTHER PUBLICATIONS

Bankmann et al. "Forming of High Surface Area TiO2 to Catalyst Supports", Catalysis Today, vol. 14, pp. 225–242, 1992.*

* cited by examiner

Primary Examiner—Stanley S. Silverman
Assistant Examiner—Colleen P. Cooke
(74) Attorney, Agent, or Firm—Muserlian, Lucas and Mercanti

(57) ABSTRACT

The invention relates to a supported catalyst and the production and use thereof in the synthesis of vinyl acetate in the gaseous phase from ethylene, acetic acid and oxygen, or from gases containing oxygen, whereby the activity and selectivity are simultaneously improved. The catalyst contains palladium, at least one alkali metal compound and optionally one or more catalyst accelerators, in particular, gold, barium and/or cadmium on a porous support. Said support contains at least one reducible metal oxide, in particular oxides of the elements of groups IIIb, IVb, Vb, VIb from the periodic table of elements. Once the support has been loaded with at least one palladium compound, a reduction is carried out at a temperature of >200° C.

13 Claims, No Drawings

CATALYSTS FOR THE GAS-PHASE OXIDATION OF ETHYLENE AND ACETIC ACID TO VINYL ACETATE, A PROCESS FOR PRODUCING THEM AND THEIR USE

This application is a 371 of PCT/EP00/02455 filed Mar. 21, 2000.

The present invention relates to highly selective catalysts for the synthesis of vinyl acetate from ethylene and acetic acid, to a process for producing them and to their use.

The preparation of vinyl acetate (VAM) in the gas phase from ethylene, acetic acid and oxygen or oxygen-containing gases is known; the supported catalysts used for this synthesis comprise Pd as active metal and an alkali metal as promoter, preferably K in the form of the acetate. Further additives used are Cd, Au or Ba.

According to U.S. Pat. Nos. 4,902,823, 3,939,199, 4,668,819 the catalytically active components are applied in finely divided form to the catalyst support by impregnation, spraying on, vapor deposition, dipping or precipitation. The procedure described gives catalysts in which the active components have penetrated to the core of the support.

However, catalysts in which the active components have not penetrated to the core but are present only in a more or less thick outer part of the support particles, i.e. the shell of the support particles, are also known (EP-A-0 565 952, EP-A-0 634 214, EP-A-0 634 209, EP-A-0 634 208).

The catalysts known from the prior art comprise, as support, the known inert support materials such as silica, aluminum oxide, aluminosilicates, silicates, titanium oxide, silicon carbide and carbon and are produced by subjecting the impregnated catalyst precursors to a reduction, e.g. in the gas phase at temperatures of 150–170° C., for example using ethylene or $H_2$, or in the liquid phase at temperatures of <100° C., e.g. using hydrazine. Higher reduction temperatures are deliberately avoided since appreciable sintering of the noble metal particles to form larger agglomerates having a lower catalytic activity occurs at temperatures >200° C.

However, it is also known that the supports impregnated with the catalytically active components can be exposed to higher temperature ranges during the course of the production of the finished catalysts. Thus, U.S. Pat. Nos. 5,336,802 and 5,194,417 describe the treatment of palladium- and gold-containing catalysts by single and multiple sequential oxidation and reduction steps.

EP-A-0 839 793 relates to a process for preparing vinyl acetate in the presence of a palladium-containing catalyst during whose production the impregnated catalyst precursor which has been treated with a reducing agent is subjected to an additional sintering step at a temperature in the range from 500 to 1000° C.

WO 98/18553 discloses calcining a palladium- and gold-containing catalyst after the impregnation step at a temperature of from 100 to 600° C. in a nonreducing atmosphere and only then carrying out the reduction step. The calcination can also be carried out in an oxygen atmosphere.

In the processes disclosed in EP-A-0 839 793 and WO 98/18553, the preparation of vinyl acetate is also carried out using supported catalysts based on inert support materials such as silica, aluminum oxide, aluminosilicates, silicates, titanium oxide, silicon carbide and carbon.

In view of the fact that catalysts are used in processes carried out on an industrial scale, for example the preparation of vinyl acetate, there is great interest in improving the catalysts, particularly in respect of their activity and selectivity.

It is therefore an object of the present invention to provide catalysts for the synthesis of vinyl acetate, which catalysts have a particularly high activity, selectivity and operating life.

A further object of the present invention is to provide catalysts which have a particularly high stability. In particular, the catalysts should be insensitive to local temperature fluctuations and hot spots and also to fluctuations in the oxygen concentration during the reaction in the synthesis of vinyl acetate and to mechanical stress.

These objects are achieved by a catalyst comprising palladium, at least one alkali metal compound and, if desired, one or more promoters on a porous support, which catalyst is obtainable by loading the porous support in which at least one reducible metal oxide is present with at least one palladium compound, subsequently carrying out a reduction at a temperature of >200° C. and additionally applying at least one alkali metal compound and, if desired, one or more promoters before or after the reduction.

The invention accordingly provides a catalyst comprising palladium, at least one alkali metal compound and, if desired, one or more promoters on a porous support and obtainable by loading the porous support in which at least one reducible metal oxide is present with at least one palladium compound, subsequently carrying out a reduction at a temperature of >200° C. and additionally applying at least one alkali metal compound and, if desired, one or more promoters before or after the reduction.

The invention further provides a process for producing catalysts, which comprises loading the porous support in which at least one reducible metal oxide is present with at least one palladium compound, subsequently carrying out a reduction at a temperature of >200° C. and additionally applying at least one alkali metal compound and, if desired, one or more promoters before or after the reduction.

The invention further provides a process for preparing vinyl acetate in the gas phase from ethylene, acetic acid and oxygen or oxygen-containing gases in the presence of a catalyst comprising palladium, at least one alkali metal compound and, if desired, one or more promoters on a porous support and obtainable by loading the porous support in which at least one reducible metal oxide is present with at least one palladium compound, subsequently carrying out a reduction at a temperature of >200° C. and additionally applying at least one alkali metal compound and, if desired, one or more promoters before or after the reduction.

In the following, the reduction of the porous support in which at least one reducible metal oxide is present and which is laden with palladium compounds at a temperature of >200° C. is referred to as the high-temperature reduction and abbreviated as HTR.

An essential aspect of the catalysts of the invention is the use of a support material in which at least one reducible metal oxide is present, for example oxides of the elements of groups IIIb, IVb, Vb, VIb of the Periodic Table of the Elements, ZnO and other reducible oxides known from the literature and also mixtures of these reducible metal oxides. Furthermore, the mixed oxides derived from the abovementioned oxides are also suitable. Preference is given to $TiO_2$ and $ZrO_2$ having intermediate to high specific surface areas as support material.

However, it is also possible to use inert support materials as such as silica, aluminum oxide, aluminum silicates, silicates, silicon carbide or carbon as long as these inert materials are first coated with the abovementioned reducible metal oxides. Such support materials are known from EP-A-723 810. The reducible metal oxide content is from 0.1 to 25% by weight, based on the total support material.

It is likewise possible to use mixtures of the reducible metal oxides with these inert materials as supports for the catalysts of the invention. Here, the proportion of the inert materials can be up to 75% by weight, based on the total support material. The proportion of the inert materials is preferably up to 50% by weight, based on the total support material.

Support materials in which at least one reducible metal oxide is present are hereinafter referred to as reducible support materials.

Surprisingly, nonreducible support materials known from the prior art, for example silica or aluminum oxide or mixtures thereof, are unsuitable for producing the catalysts of the invention. Oxides which can be reduced to the metal under the production conditions employed according to the invention are likewise unsuitable as support materials.

The reducible support can be used either in powder form or as shaped bodies. The support material is preferably used as shaped bodies and is in the form of pellets, spheres, tablets, rings, extrudates, ribbed extrudates, star extrudates, stars, hollow extrudates or other industrial shaped bodies. The diameter or the length and thickness of the support materials is generally from 3 to 9 mm. The surface area of the support measured by the BET method is generally 10–500 $m^2/g$, preferably 15–250 $m^2/g$. The pore volume is generally from 0.2 to 1.2 ml/g. The pore volume is determined by means of mercury porosimetry.

The support materials employed according to the invention can be produced by any method known to those skilled in the art. They are generally commercially available.

Loading a reducible support with at least one palladium compound and subsequently carrying out a high-temperature reduction at temperatures of >200° C. and additionally applying at least one alkali metal compound and, if desired, one or more promoters before or after the reduction gives catalysts which have an excellent activity and selectivity and also excellent adhesion of noble metal to the support.

The novel measure of the HTR of porous reducible supports laden with palladium compounds is carried out at temperatures of >200° C., preferably >300° C.

If desired, one or more promoters are subsequently applied to the support which has been loaded in this way. Preference is given to using at least one Au, Ba or Cd compound or a mixture of these compounds.

However, the addition of promoters is preferably carried out before the HTR treatment, either in admixture with the palladium compound or compounds or separately therefrom. The order plays no role; the porous reducible support can be loaded first with the palladium compound and then with the promoters or vice versa.

The catalysts of the invention further comprise at least one alkali metal compound, preferably at least one potassium compound. The addition of alkali metal to the porous reducible support can be carried out prior to the HTR treatment, either separately or in admixture with the other promoters and/or with the palladium compound or compounds, or after the HTR treatment, either separately or in admixture with the other promoters.

Finally, the catalysts of the invention can be finished in accordance with the prior art and used in industrial processes, for example in the synthesis of vinyl acetate.

According to the invention, the reducible support material is first loaded with a palladium compound. The type of compound is not critical here, as long as high dispersion of the metal can be achieved. Soluble palladium compounds are suitable for this purpose, in particular water-soluble salts. Preference is given to, for example, palladium compounds selected from the group consisting of palladium(II) acetate, palladium(II) chloride, sodium tetrachloropalladate (II) [$Na_2PdCl_4$] and palladium(II) nitrate. Besides palladium (II) acetate, further carboxylates of palladium can be used, preferably the salts of aliphatic monocarboxylic acids having from 3 to 5 carbon atoms, for example the propionate or butyrate.

However, in the case of the chlorides, it has to be ensured that the chloride ions are removed to leave a tolerable residual amount before use of the catalyst. For this purpose, the catalyst support is washed with water after loading with palladium compounds and with the promoters and after the HTR. This is achieved by washing the support, e.g. with water, after Pd and, if used, Au have been fixed to the support by reduction to the metals.

The palladium compounds mentioned can be prepared by any method known to those skilled in the art. However, most of them are also commercially available.

Promoters used are compounds of the elements Au, Ba and Cd, in particular soluble salts of these elements.

Suitable gold compounds include, for example, tetrachloroauric(III) acid [$HAuCl_4$], gold(III) acetate [$Au(OAc)_3$], potassium aurate [$KAuO_2$]. It is advisable to prepare the gold acetate or the potassium aurate freshly by precipitation of the oxide/hydroxide from solutions of tetrachloroauric acid, washing and isolating the precipitate and taking it up in acetic acid or KOH. The gold compounds are preferably applied to the support before the high-temperature reduction.

Suitable cadmium compounds include, for example, cadmium acetate $Cd(OAc)_2$ and other carboxylates of cadmium, for example the propionate or butyrate. The cadmium compounds can be applied to the support either before or after the high-temperature reduction.

Suitable barium compounds include, for example, barium acetate $Ba(OAc)_2$, other barium carboxylates such as the propionate or butyrate and also barium hydroxide $Ba(OH)_2$. The barium compounds can be applied to the support either before or after the high-temperature reduction.

The catalyst of the invention further comprises at least one alkali metal compound, preferably at least one potassium or rubidium compound and particularly preferably at least one potassium compound. Suitable potassium compounds include, for example, potassium acetate KOAc, potassium carbonate $K_2CO_3$, potassium hydrogen carbonate $KHCO_3$ and potassium hydroxide KOH, and also all potassium compounds which are converted into the acetate under the reaction conditions. The potassium compounds can be applied to the support either before or after the high-temperature reduction.

Preference is given to using the acetates for loading the porous reducible support since these catalysts cause very little chloride contamination.

The metal compounds are usually used in concentrations of from about 0.1 to 100 g per liter, preferably from 1 to 50 g per liter, based on the solvent.

Suitable solvents are all compounds in which the compounds or salts chosen are soluble and which can be easily removed again by drying after the impregnation. Examples of suitable solvents for the acetates are, in particular, unsubstituted carboxylic acids, especially acetic acid, while the chlorides are soluble primarily in water or dilute hydrochloric acid.

If the salts are not sufficiently soluble in acetic acid or in water, the additional use of a further solvent in addition to water or acetic acid, which are also used as a mixture, can be advantageous.

Possible additional solvents are ones which are inert and miscible with acetic acid or water. Examples of additions to acetic acid are ketones such as acetone and acetylacetone, also ethers such as tetrahydrofuran or dioxane, acetonitrile, dimethylformamide and also hydrocarbons such as benzene.

The application of the active component Pd and the further promoters and also the alkali metal compound can be carried out by the methods known from the prior art.

The finished catalysts have the following metal contents, expressed in gram of metal per 1 l of finished catalyst:

| Palladium: | generally | 1–20 g/l |
|---|---|---|
| | preferably | 3–15 g/l |
| | in particular | 5–10 g/l |
| Alkali metal content: | generally | 5–30 g/l |
| | preferably | 10–25 g/l |
| | in particular | 10–16 g/l |

If the finished catalyst further comprises one or more promoters, the promoter content is in each case generally up to 20 g/l, preferably 2–15 g/l and in particular 3–10 g/l.

In the synthesis of vinyl acetate, preference is given to using the catalyst systems based on Pd/Cd/K, Pd/Ba/K or Pd/Au/K. Particular preference is given to systems comprising Pd—Au—K. It is an essential aspect of the present invention that at least Pd and possibly Au are subjected to the HTR, while the other promoters such as the potassium compounds and further additives can be added either before or after the HTR.

It is found that the catalysts of the invention are superior to the catalysts known from the prior art in respect of activity and particularly in respect of the selectivity in industrial processes. An example of an important industrial process of this type is the synthesis of vinyl acetate.

The use of the catalysts of the invention in the synthesis of vinyl acetate has, in particular, the following advantages:

Surprisingly, a selectivity increase of more than 5% is achieved, which is measurable by a drastic reduction in the undesirable total oxidation to $CO_2$.

At the same time, an activity increase of more than 20% compared to catalysts known from the prior art is achieved.

The novel measure of the HTR induces a very strong interaction between the noble metal particles and the reducible support and this interaction effects an advantageous change in the properties of the noble metal particles for catalysis and is responsible for excellent mechanical anchoring to the support and thus a high agglomeration resistance.

The high-temperature-reduced catalysts of the invention have a particularly uniform Pd/Au active metal distribution and a high degree of dispersion of the noble metals.

The high degree of dispersion is largely maintained even in long-term operation owing to reduced agglomeration of the noble metal particles, as a result of which the deactivation of the catalysts of the invention is slowed and long operating lives are achieved.

In addition, the catalysts of the invention have excellent mechanical stabilities since the chemically reactive reducible supports can easily be shaped to produce mechanically hard shaped bodies and the HTR at high temperatures further increases the hardness of the shaped bodies.

The catalysts of the invention are insensitive to hot spots and also to fluctuations in the oxygen concentration during the reaction of the vinyl acetate synthesis, and the intensity of the hot spots is greatly reduced owing to the extraordinarily high selectivity (drastic reduction in the strongly exothermic total oxidation to CO or $CO_2$), as a result of which regulation and process control are significantly simplified.

Since an increase in the space-time yield (STY) accompanies a selectivity increase, particularly high throughputs can be realized in large plants.

Achievement of the abovementioned advantages could not have been foreseen from the prior art, since the prior art puts forward the opinion that reduction temperatures of >200° C. are damaging and, owing to agglomeration of the noble metal particles, reduce the activity. Thus, hot spots of >190° C. are avoided if possible both in the conventional reduction and later in operation.

Furthermore, the prior art teaches the use of inert supports such as silicon dioxide or silicon dioxide/aluminum oxide mixtures, preferably silicon dioxide.

Loading of the support with the desired amounts of the respective compounds can be carried out in one step or a plurality of sequential steps, with drying steps being able, if desired, to be inserted between the individual steps.

It is possible, for example, to apply one compound, e.g. a salt, of each of the elements to be applied to the support particles, e.g. Pd/K/Au, Pd/K/Cd or Pd/K/Ba. However, a plurality of salts of one element can also be applied or mixed compounds of the various metals can be used. In general, exactly one salt of each of the three elements is used.

The salts can be applied to the support by known loading methods, for example steeping, impregnation, spraying on, vapor deposition, dipping or precipitation. The support can be impregnated right through with the salts or it is possible to use all methods known to those skilled in the art which are employed for producing surface-impregnated catalysts. These are disclosed, for example, in the documents DE-A-1 668 088, U.S. Pat. No. 3,775,342, U.S. Pat. No. 3,822,308, U.S. Pat. No. 4,048,096, U.S. Pat. No. 5,185,308, U.S. Pat. No. 5,567,839, U.S. Pat. No. 5,314,858, EP-A-0 634 208, EP-A-0 634 209 or EP-A-0 634 214.

In the case of the Pd/Au/K catalysts, it has been found to be advantageous to apply the two noble metals in the form of a shell on the support, i.e. the noble metals are distributed only in a zone close to the surface while the regions further inside the support body are virtually free of noble metals. The thickness of this catalytically active shell is usually 0.1–2 mm.

In many cases, surface-impregnated catalysts make possible a more selective process than is the case for catalysts in which the support particles are impregnated to the core ("fully impregnated").

If the reaction conditions when using surface-impregnated catalysts are left unchanged from the reaction conditions when using fully impregnated catalysts, more vinyl acetate can be produced per unit reactor volume and time, which equates to a capacity increase without additional capital costs. The work-up of the crude vinyl acetate obtained is also made easier, since the vinyl acetate content of the product gas from the reactor is higher, which also leads to an energy saving in the work-up. Suitable work-up processes are described, for example, in U.S. Pat. No. 5,066,365, DE-34 22 575, DE-A-34 08 239, DE-A-29 45 913, DE-A-26 10 624, U.S. Pat. No. 3,840,590.

If, on the other hand, the plant capacity is kept constant, the reaction temperature can be lowered and the reaction can therefore be carried out more selectively at the same total output, thus saving starting materials. This also reduces the amount of carbon dioxide which is formed as by-product and therefore has to be discharged and decreases the loss of entrained ethylene associated with this discharge.

Furthermore, this operating procedure leads to a lengthening of the operating life of the catalyst.

According to the invention, the catalyst has to be subjected to a high-temperature reduction after loading with at least one palladium compound.

For this purpose, a vaporizable or gaseous reducing agent can be passed at temperatures of above 200° C., preferably in the range from 200° C. to 700° C. and particularly preferably in the range from 300° C. to 600° C., over the loaded catalyst.

Suitable reducing agents for the HTR are all materials which are able to reduce the palladium compounds and, if used, gold compounds to the metals at the high reduction temperatures employed according to the invention.

Preference is given to gaseous or vaporizable reducing agents for example $H_2$, CO, ethylene, $NH_3$, formaldehyde, methanol and hydrocarbons in general and also mixtures of these reducing agents. Hydrogen is particularly preferred.

The gaseous reducing agents can also be diluted with inert gas, for example carbon dioxide, nitrogen or argon. Preference is given to using a reducing agent diluted with inert gas. Mixtures of hydrogen with nitrogen or argon, preferably those having a hydrogen content of from 1% by volume to 15% by volume, are preferred.

The reduction times are generally in the range from 1 minute to 24 hours, particularly preferably from 30 minutes to 10 hours.

The amount of reducing agent is selected so that at least the number of equivalents of reducing agent required for complete reduction of the noble metals are passed over the catalyst during the treatment time. Preference is given to passing an excess of reducing agent over the catalyst in order to ensure complete reduction. The volume flow of reducing gas is calculated from the pressure employed in the reduction, the dilution and the reaction time. Preference is given to carrying out the reduction at atmospheric pressure, i.e. at an absolute pressure of about 1 bar. For the production of industrial amounts of the catalyst of the invention, preference is given to using a rotary tube furnace or a fluidized-bed reactor in order to ensure uniform reduction of the catalyst.

In the reduction according to the invention, it is first and foremost the noble metal compounds, i.e. Pd and for example Au, which are reduced to the corresponding metals, with the support material being partially reduced, e.g. to form $Ti^{3+}$ centers in the $TiO_2$ lattice. In contrast thereto, the other metal compounds present, i.e. the alkali metal compounds and the other promoters apart from gold, are generally not reduced. For this reason, the alkali metal compounds and the nonreducible promoters can be applied to the support either before or after the high-temperature reduction.

In a preferred embodiment of the invention, $TiO_2$ or $ZrO_2$ supports or mixtures thereof or mixtures with further inert support constituents, for example $SiO_2$ and/or $Al_2O_3$, preferably as shaped bodies, more preferably in the form of pellets, spheres, rings, extrudates or tablets, are impregnated with palladium acetate and gold acetate, dried and reacted with gaseous reducing agents, preferably $H_2$, ethylene and/or $NH_3$, in the HTR in the temperature range of 200–700° C., preferably 300–600° C., for a period ranging from 1 minute to 10 hours. If desired, this is followed by impregnation with potassium acetate and final drying at a temperature of not more than 150° C., preferably 80–150° C. and in particular 100–150° C.

However, it is also possible to use support materials in which the inert support constituents have firstly been coated with $TiO_2$ or $ZrO_2$ or with a mixture of these oxides. This is followed by the impregnation step and the HTR. The proportion of $TiO_2$ or $ZrO_2$ is from 0.1 to 25% by weight, based on the support material.

Further pretreatment or after-treatment steps which are known to those skilled in the art can be inserted. These include, inter alia, washing, drying, calcination, oxidation and/or reduction.

The catalysts of the invention are preferably used for preparing vinyl acetate. This is generally carried out by passing acetic acid, ethylene and oxygen or oxygen-containing gases at temperatures of from 100 to 220° C., preferably from 120 to 200° C., and pressures of from 1 to 25 bar, preferably from 1 to 20 bar, over the finished catalyst, with unreacted components being able to be circulated. The oxygen concentration is advantageously kept below 10% by volume (based on the gas mixture excluding acetic acid). However, dilution with inert gases such as nitrogen or carbon dioxide is sometimes also advantageous. Carbon dioxide is particularly suitable for dilution, since it is formed in small amounts during the reaction. The vinyl acetate formed is isolated by means of suitable methods as are described, for example, in U.S. Pat. No. 5,066,365, DE-A-34 22 575, DE-A-34 08 239, DE-A-29 45 913, DE-A-26 10 624, U.S. Pat. No. 3,840,590.

The following examples serve to explain and illustrate the invention without restricting it thereto.

EXAMPLE 1

2.11 g of palladium acetate (224.49 g/mol) and 1.32 g of gold acetate (374.10 g/mol) were dissolved in 30 ml of glacial acetic acid. The preparation of gold acetate is described, for example, in U.S. Pat. No. 4,933,204. 100 ml of $TiO_2$ supports (P25 pellets, DEGUSSA) were added to this solution. Subsequently, the major part of the glacial acetic acid was firstly distilled off at 70° C. on a rotary evaporator, residues of solvent were then removed at 60° C. with the aid of an oil pump and finally in a vacuum drying oven for a period of 14 hours, likewise at 60° C.

The reduction was carried out using a gas mixture of 10% by volume of $H_2$ in $N_2$. Here, the gas was passed at a temperature of about 500° C. through the pellets for one hour. The reduction was carried out under atmospheric pressure at a flow of 40 l/h of a mixture of 10% by volume of $H_2$ in nitrogen. To load them with potassium ions, the pellets were treated with a solution of 4 g of potassium acetate in 30 ml of water. This mixture was allowed to act on the pellets at room temperature for 15 minutes in a mixer. The solvent was subsequently removed on a rotary evaporator. The pellets were dried for 14 hours at 110° C. in a drying oven.

The catalyst comprised: 7 g/l Au; 16 g/l K; <1 g/l Cl; 10 g/l Pd.

The production of the catalyst was repeated twice. The testing of these catalysts in the synthesis of vinyl acetate is reported as Examples 1A to 1C in Table 1 below.

EXAMPLE 2

2.11 g of palladium acetate (224.49 g/mol) and 1.32 g of gold acetate (374.10 g/mol) were dissolved in 45 ml of glacial acetic acid. 100 ml of $TiO_2$ supports (XT25376 pellets, Norton) were added to this solution. Subsequently, the major part of the glacial acetic acid was firstly distilled off at 70° C. on a rotary evaporator, residues of solvent were then removed at 60° C. with the aid of an oil pump and finally in a vacuum drying oven for a period of 14 hours, likewise at 60° C.

The reduction was carried out using a gas mixture consisting of 10% by volume of $H_2$ in $N_2$. Here, the gas was passed at a temperature of about 500° C. through the pellets for 1 hour. The reduction was carried out under atmospheric pressure at a flow of 40 l/h of a mixture of 10% by volume of $H_2$ in nitrogen. To load them with potassium ions, the pellets were treated with a solution of 4 g of potassium acetate in 45 ml of water. The pellets which had been impregnated in this way were mixed for 10 minutes at room temperature. The solvent was subsequently removed on a rotary evaporator. The pellets were dried for 14 hours at 110° C. in a drying oven.

The catalyst comprised: 7 g/l Au; 16 g/l K; <1.1 g/l Cl; 10 g/l Pd.

EXAMPLES 3A–C 2.11 g of palladium acetate (224.49 g/mol), 1.32 g of gold acetate (374.10 g/mol) and 4.0 g of potassium acetate were dissolved in 30 ml of glacial acetic acid. 100 ml of $TiO_2$ supports (P25 pellets, DEGUSSA) were added to this solution. Subsequently, the major part of the glacial acetic acid was firstly distilled off at 60° C. on a rotary evaporator and residues of solvent were then removed at 60° C. in a vacuum drying oven over a period of 4 hours.

The batch was divided into three parts which were subjected to different reduction conditions.

| Batch | Time | Temperature | Reducing agent |
|-------|------|-------------|----------------|
| A | 4 h | 400° C. | 10% by volume of $H_2$ in $N_2$ |
| B | 4 h | 450° C. | 10% by volume of $H_2$ in $N_2$ |
| C | 4 h | 500° C. | 10% by volume of $H_2$ in $N_2$ |

The reduction was carried out using a gas mixture consisting of 10% by volume of $H_2$ in $N_2$. Here, the gas was passed at a temperature of about 400° C. (batch A), 450° C. (batch B) or 500° C. (batch C) through the pellets for 4 hours in each case. The reduction was carried out under atmospheric pressure at a flow of 40 l/h.

The catalyst comprised: 7 g/l Au; 16 g/l; <1.5 g/l Cl; 10 g/l Pd.

EXAMPLE 4

1.06 g of palladium acetate (224.49 g/mol), 0.66 g of gold acetate (374.10 g/mol) and 2.0 g of potassium acetate were dissolved in 15 ml of glacial acetic acid. 50 ml of $TiO_2$ supports (P25 pellets, DEGUSSA) were added to this solution. Subsequently, the major part of the glacial acetic acid was firstly distilled off at 60° C. on a rotary evaporator and residues of solvent were then removed at 60° C. for 14 hours in a vacuum drying oven.

The reduction was carried out at 500° C. for 1 hour using a gas mixture consisting of 10% by volume of $H_2$ in $N_2$, using a method similar to Example 1.

The catalyst contained: 7 g/l Au; 16 g/l K; <1 g/l Cl; 10 g/l Pd.

EXAMPLE 5

1.06 g of palladium acetate (224.49 g/mol), 0.66 g of gold acetate (374.10 g/mol) and 4.0 g of potassium acetate were dissolved in 30 ml of glacial acetic acid at 60° C. 100 ml of $TiO_2$ supports (P25 pellets, DEGUSSA) were added to this solution. Subsequently, the major part of the glacial acetic acid was firstly distilled off at 60° C. on a rotary evaporator and residues of solvent were then removed at 60° C. for 4 hours using an oil pump.

The reduction was carried out at 500° C. for 1 hour using a gas mixture consisting of 10% by volume of $H_2$ in $N_2$, using a method similar to Example 1.

The catalyst contained: 3.5 g/l Au; 16 g/l K; <0.5 g/l Cl; 5 g/l Pd.

COMPARATIVE EXAMPLE 1

1.82 g of $Na_2PdCl_4$ (294.19 g/mol) and 0.64 g of $NaAuCl_4$ (361.76 g/mol) were dissolved in 32 ml of demineralized water. This solution was applied completely to 100 ml of $SiO_2$ supports (KA160 pellets, Süd-Chemie) with gentle agitation. To form a noble metal shell, the pretreated support was placed in a solution of 0.85 g of sodium hydroxide, NaOH, in 32 ml of demineralized water. The reaction mixture was left to stand overnight and the pellets were then washed free of chloride using demineralized water.

The catalyst was then reduced with an ethylene/nitrogen mixture (5% of ethylene in nitrogen) at 150° C. for 5 hours.

To load the pellets with potassium ions, they were treated with a solution of 4 g of potassium acetate in 30 ml of water and the finished catalyst was dried for 2 hours in a rapid drier.

The catalyst comprised: 3.5 g/l Au; 16 g/l K; <0.5 g/l Cl; 6.6 g/l Pd.

COMPARATIVE EXAMPLE 2

1.06 g of palladium acetate (224.49 g/mol), 0.7 g of gold acetate (374.10 g/mol) and 4.0 g of potassium acetate were dissolved in 30 ml of glacial acetic acid at 60° C. 100 ml of $TiO_2$ supports (P25 pellets, DEGUSSA) were added to this solution. Subsequently, the major part of the acetic acid was firstly distilled off at 60° C. on a rotary evaporator and residues of solvent were then removed at 60° C. over a period of 4 hours using an oil pump.

Reduction was carried out using a gas mixture consisting of 10% by volume of $H_2$ and 90% by volume of $N_2$, in each case based on the volume, at 170° C. for 1 hour (atmospheric pressure, gas flow: 40 l/h).

The catalyst comprised: 3.5 g/l Au; 16 g/l K; <0.5 g/l Cl; 5 g/l Pd.

COMPARATIVE EXAMPLE 3

0.53 g of palladium acetate (224.49 g/mol), 0.33 g of gold acetate (374.10 g/mol) and 2.0 g of potassium acetate were dissolved in 30 ml of glacial acetic acid. 50 ml of $TiO_2$ supports (XT25376 pellets, Norton) were added to this solution. Subsequently, the major part of the glacial acetic acid was firstly distilled off at 70° C. on a rotary evaporator, residues of solvent were then removed at 60° C. with the aid of an oil pump and finally in a vacuum drying oven for a period of 14 hours, likewise at 60° C.

The reduction was carried out thermally without reducing gas (autoreduction). Here, nitrogen as flushing gas was passed through the pellets for 1 hour at a temperature of about 500° C. (atmospheric pressure, 40 l/h)

The catalyst comprised: 3.5 g/l Au; 16 g/l K; <0.5 g/l Cl; 5 g/l Pd.

COMPARATIVE EXAMPLE 4

1.06 g of palladium acetate (224.49 g/mol), 0.7 g of gold acetate (374.10 g/mol) and 4.0 g of potassium acetate were dissolved in 80 ml of glacial acetic acid at 60° C. 100 ml of $SiO_2$ supports (Aerosil 200 pellets, DEGUSSA) were added to this solution. Subsequently, the major part of the glacial acetic acid was firstly distilled off at 60° C. on a rotary evaporator and residues of solvent were then removed at 60° C. over a period of 4 hours using an oil pump.

The reduction was carried out using a gas mixture consisting of 10% by volume of $H_2$ in $N_2$ for 1 hour at 500° C., using a method similar to Example 1.

The catalyst comprised: 3.5 g/l Au; 16 g/l K; <0.5 g/l Cl; 5 g/l Pd.

COMPARATIVE EXAMPLE 5

1.06 g of palladium acetate (224.49 g/mol), 0.7 g of gold acetate (374.10 g/mol) and 4.0 g of potassium acetate were dissolved in 80 ml of glacial acetic acid at 60° C. 100 ml of $SiO_2$ supports (KA160 pellets, Süd-Chemie) were added to this solution. Subsequently, the major part of the glacial acetic acid was firstly distilled off at 60° C. on a rotary evaporator and residues of solvent were then removed at 60° C. over a period of 4 hours using an oil pump.

The reduction was carried out using a gas mixture consisting of 10% by volume of $H_2$ in $N_2$ for 1 hour at 500° C., using a method similar to Example 1.

The catalyst comprised: 3.5 g/l Au; 16 g/l K; <0.5 g/l Cl; 5 g/l Pd.

Reactor tests for the gas-phase oxidation of ethylene and acetic acid to vinyl acetate:

The catalysts produced in the examples and comparative examples are tested in a fixed-bed tube reactor having a tube diameter of 2 cm. The reactor is heated externally by means of oil jacket heating. The reactor is typically charged with 15 ml of the shaped catalyst bodies. The reactor volume upstream and downstream of the catalyst bed is filled with glass spheres to reduce the dead volume. The gases are meted in via mass flow regulators for gases; the acetic acid is meted in using a mass flow regulator/vaporizer unit. The gases and the acetic acid are mixed in a packed gas mixing tube. The test apparatus is operated continuously.

The reaction is monitored continually by means of a gas chromatograph.

When a steady-state reaction has been achieved, i.e. the reactor temperature is constant and the concentrations of vinyl acetate and $CO_2$ in the product gas stream are constant, the recording of data is commenced.

The experiments were carried out using a reaction temperature in the range 150–170° C. and a reaction pressure of 8–9 bar. The composition of the starting material stream was typically 60–80% by volume of ethylene, 10–20% by volume of $N_2$, 10–20% by volume of acetic acid and 2–10% by volume of $O_2$. A complete analysis of the output from the reactor was carried out directly at the reactor outlet by means of on-line GC (2 column arrangement) and on-line IR.

The GC data were used to calculate the vinyl acetate selectivities S (=mol of VAM/(mol of VAM+0.5* mol of $CO_x$, X=1 or 2) and STY (space-time yield=g of VAM/1 of cat. *h). Table 1 shows the results of the individual experiments in which the catalysts prepared in Examples 1 to 5 were tested.

TABLE 1

Testing of the catalysts in the synthesis of vinyl acetate

| Example No. | T (° C.) | p (bar) | $O_2$ conc. (%) | S % | STY g/l*h |
|---|---|---|---|---|---|
| 1A | 170 | 9 | 5.2 | 96 | 1000 |
|  | 160 | 9 | 5.2 | 98 | 1050 |
|  | 155 | 9 | 5.2 | 98 | 1000 |
| 1B | 170 | 9 | 5.2 | 97 | 700 |
|  | 160 | 9 | 5.2 | 98 | 1150 |
| 1C | 170 | 9 | 5.2 | 98 | 1300 |
| 2 | 170 | 9 | 5.2 | 96 | 1200 |
| 3A | 160 | 9 | 5.2 | 89 | 1400 |
|  | 150 | 9 | 5.2 | 98 | 1400 |
| 3B | 160 | 9 | 5.2 | 95 | 1260 |
| 3C | 160 | 9 | 5.2 | 96 | 1210 |
| 4 | 150 | 9 | 5.2 | 96 | 1100 |
| 5 | 160 | 9 | 5.2 | 95 | 940 |
| Comp. 1 | 170 | 9 | 5.1 | 88 | 850 |
| Comp. 2 | 160 | 9 | 5.2 | 80 | 870 |
| Comp. 3 | 170 | 9 | 5.2 | 77 | <50 |
| Comp. 4 | 167 | 9 | 5.2 | 89 | 190 |
| Comp. 5 | 170 | 9 | 5.2 | 83 | 340 |

It can be seen from the table that the HTR treatment of catalysts in which a reducible support material is present significantly improves the selectivity and yield in the vinyl acetate synthesis compared to the catalysts known from the prior art.

What is claimed is:

1. A catalyst comprising palladium, at least one alkali metal compound and, optionally, at least one promoter on a porous support, obtained by the steps consisting essentially of loading the porous support, with at least one palladium compound which support comprises $TiO_2$ produced through the flame hydrolysis of $TiCl_4$, reducing the loading support, at a temperature of 300–500° C. and then applying at least one alkali metal compound and, optionally, at least one promoter before or after the reduction.

2. A catalyst of claim 1 which comprises at least one potassium compound.

3. A catalyst of claim 1 which additionally comprises at least one member of the group consisting of Au, Ba, Cd and their compounds as promoter.

4. A catalyst of claim 1, wherein the reduction is carried out for 1 minute to 24 hours.

5. A catalyst of claim 1, wherein the reduction is carried out using gaseous or vaporizable reducing agents.

6. A catalyst of claim 1, wherein the reducing agent for the reduction is at least one member selected from the group consisting of $H_2$, CO, ethylene, $NH_3$, formaldehyde, methanol, hydrocarbons and mixtures of these reducing agents with inert gases.

7. A process for producing a catalyst of claim 1, comprising the steps consisting essentially of loading the porous support with at least one palladium compound, which support comprises $TiO_2$ produced through the flame hydrolysis of $TiCl_4$, reducing the loaded support at a temperature of 300–500° C. and then applying at least one alkali metal compound and, optionally, at least one promoter before or after the reduction.

8. The process of claim 7, wherein the catalyst comprises at least one potassium compound.

9. The process of claim 7, wherein the catalyst additionally comprises at least one member of the group consisting of Au, Ba, Cd and their compounds as promoters.

10. The process of claim 7, wherein the reduction is carried out from 1 minute to 24 hours.

11. The process of claim 7, wherein the reduction is carried out using gaseous or vaporizable reducing agents.

12. The process of claim 7, wherein the reducing agent for the reduction is at least one member selected from the group consisting of $H_2$, CO, ethylene, $NH_3$, formaldehyde, methanol, hydrocarbons and mixtures of these reducing agents with inert gases.

13. In a process for the preparation of vinyl acetate from the gaseous phase reaction of ethylene, acetic acid and oxygen or oxygen containing gas, the improvement comprising using as catalyst the catalyst of claim 1.

* * * * *